United States Patent [19]

Weber

[11] 4,137,126

[45] Jan. 30, 1979

[54] PROCESS FOR PREPARING GLUCOSE ISOMERASE USING *STREPTOMYCES GLAUCESCENS* MUTANTS

[75] Inventor: Peter Weber, Greifensee, Switzerland

[73] Assignee: Givaudan Corporation, Clifton, N.J.

[21] Appl. No.: 851,332

[22] Filed: Nov. 14, 1977

Related U.S. Application Data

[63] Continuation of Ser. No. 680,608, Apr. 26, 1976, abandoned.

[30] Foreign Application Priority Data

May 3, 1975 [CH] Switzerland ............... 5702/75

[51] Int. Cl.$^2$ ............... C12D 13/10; C12D 13/02
[52] U.S. Cl. ............... 195/66 R; 195/31 F; 195/62; 195/65
[58] Field of Search ............... 195/31 F, 65, 62, 66 R

[56] References Cited

U.S. PATENT DOCUMENTS

| 3,753,858 | 8/1973 | Takasaki et al. ............... 195/31 F |
| 3,813,318 | 5/1974 | Armbruster et al. ............... 195/31 F |

FOREIGN PATENT DOCUMENTS 2408708  9/1974  Fed. Rep. of Germany ......... 195/31 F

*Primary Examiner*—Thomas G. Wiseman
*Attorney, Agent, or Firm*—Thomas Cifelli, Jr.; Robert F. Tavares

[57] ABSTRACT

Use of certain mutants of *Streptomyces glaucescens* NRRL B-2900 or glucose-isomerases thereof results in improved process for isomerizing glucose to fructose.

10 Claims, No Drawings

PROCESS FOR PREPARING GLUCOSE ISOMERASE USING *STREPTOMYCES GLAUCESCENS* MUTANTS This is a continuation, of application Ser. No. 680,608 filed Apr. 26, 1976 now abandoned.

FIELD OF THE INVENTION

This invention relates to the isomerization of glucose to fructose in the presence of microorganisms.

SUMMARY OF THE INVENTION

The present invention is concerned with an improved process for the manufacture of fructose by the isomerisation of glucose, which process comprises carrying out the isomerisation using a mutant of *Streptomyces glaucescens* NRRL B-2900 having no or practically no intra-cellular tyrosinase activity, or a glucose-isomerase isolated therefrom.

It is known that various microorganisms such as, for example, members of the genera Streptomyces, Bacillus, Lactobacillus, Aerobacter, Nocardia, Actinoplanes or Pseudomonas, are capable of isomerising glucose to fructose by means of a glucose-isomerase. Amongst the Streptomycetes, the species *olivochromogenes, wedmorensis, olivaceus, venezuelae, phaechromogenes, albus* and *rubiginosus* are, after induction with xylose, above all capable of producing a glucose-isomerase.

Recently, it has also been found (see German Offenlegungsschrift No. 2 408 708) that the known microorganism *Streptomyces glaucescens*, especially the strain NRRL B-2900 (ETH 22794), [described in "Systematik der Streptomyceten unter besonderer Berücksichtigung der von ihnen gebildeten Antibiotika," R. Hütter, Verlag S. Karger. Basel and New York, Bibl. Mikrobiol. 6 (1967), 90–92], is capable of synthesising a glucose-isomerase on a suitable nutrient base, very high proportions of extra-cellular glucose-isomerase being produced.

It has now surprisingly been found in accordance with the present invention that certain mutants of *Streptomyces glaucescens* NRRL B-2900 are significantly better for the such which has no or practically no intra cellular tyrosinase activity.

These mutants are superior to the microorganisms hitherto used for the isomerisation of glucose for the following reasons:

The enzyme preparations obtained therefrom provide very high specific activities. Since, by definition, the mutants have no or practically no intra-cellular tyrosinase activity, the microorganism also forms no melanine (pigment) during the growth in the nutrient medium and therefore colorations during the growth, which would lead to impure fructose products in the subsequent isomerisation process do not occur. In particular, however, the said mutants are characterised in that they produce very high portions of intra-cellular glucose-isomerase. This is especially desired since today interest turns more and more to fixed enzymes, namely to enzymes which are preferably fixed in the cell (mycelium). In the isomerisation of glucose to fructose, an advantage is thus realised, namely that expensive and necessary isolations and purifications of the enzymes can be omitted. Furthermore, the enzyme preparations obtained are very stable, i.e. inactivations, especially irreversible inactivations (denaturing), during the isomerisation of glucose hardly occur so that the preparations can be used for several isomerisations. This, of course, leads to increased economy.

Finally, a further advantage of the mutants defined earlier consists in that they only lyse slightly.

DESCRIPTION OF THE PREFERRED EMBODIMENTS

The present invention is based on the foregoing finding and is accordingly concerned with a process for the manufacture of fructose by the isomerisation of glucose, which process comprises carrying out the isomerisation using a mutant of *Streptomyces glaucescens* NRRL B-2900 having no or practically no intra-cellular tyrosinase activity or a glucose-isomerase isolated therefrom.

The invention is also concerned with a process for the manufacture of a glucose-isomerase, which process comprises cultivating a mutant of *Streptomyces glaucescens* NRRL B-2900 having no or practically no intra-cellular tyrosinase activity in a nutrient medium and, if desired, isolating the glucose-isomerase therefrom.

By the term "mutants having practically no intra-cellular tyrosinase activity" there are to be understood mutants which form enzymes having a specific activity $\leq 0.01$ units per mg of protein. This activity is preferably determined by means of the dopachrome test of L. Lerch and L. Ettlinger [see Eur. J. Biochem. 31, 427–437 (1972): Purification and Characterisation of a Tyrosinase from *Streptomyces glaucescens*.].

Preferred strains used in the present invention are *Streptomyces glaucescens* NRRL 8071, 8072, 8073 and 8074.

The foregoing four strains have been deposited at the Northern Regional Research Laboratory U.S. Department of Agriculture, Peoria, Ill.

These melanine-negative mutants can be produced using customary mutagenic agents, for example according to R. Baumann et al., described in "Actinomycetes, The boundary microorganisms" (ed. T. Arai) Toppon. Co. Ltd., Tokyo (1975), in press, by acridine-orange treatment [D. H. Bonanchaud et al., J. gen. Microbiol. 54, 417–425 (1969)] or by ultraviolet as well as Röntgen irradiation of spore or mycelium suspensions. Apart from such mutants produced by induction, mutation can also occur spontaneously as is known. The melanine-negative mutants may be identified and isolated by the absence of melanine formation on tyrosine agar or peptone/yeast extract/iron agar:

| | Auxotrophy for | Mutation production with respect to melanine formation |
|---|---|---|
| *Str. glaucescens* NRRL 8071 | — | spontaneous |
| *Str. glaucescens* NRRL 8072 | methionine, lysine | induced |
| *Str. glaucescens* NRRL 8073 | histidine | induced |
| *Str. glaucescens* NRRL 8074 | lysine, nicotinic acid | induced |

The cultivation of the microorganisms used in the present invention can be carried out in a manner known per se under aerobic conditions, preferably in submerged cultures, using fermenters.

A suitable nutrient medium, which can be solid or liquid, contains a source of assimilable carbon and a source of assimilable nitrogen as well as, expediently, mineral salts and trace elements. Suitable sources of assimilable carbon are, for example, malt extract, starch, glucose, maltose and saccharose as well as other sugars, glycerine, amino acids, peptides and fatty acids. Suitable sources of assimilable nitrogen are microbial, vegetable, animal and inorganic nitrogen compounds such as yeast extract, peptone, bactotryptone, meat extract, amino acids, pancreatic or acid-hydrolysed casein, soya-bean meal, cornsteep liquor, sodium nitrate and ammonium sulphate. Finally, the presence of elements such as, for example, magnesium, phosphorus, sulphur, cobalt and manganese, is advantageous for a good growth. There can also be added according to requirement or desire, special growth factors or stimulants (e.g. vitamins such as biotin or pyridoxin or auxines).

A suitable nutrient medium has, for example, the following composition:

| Yeast extract | 20.00 g |
|---|---|
| Potassium hydrogen phosphate trihydrate | 0.5 g |
| Magnesium sulphate heptahydrate | 0.25 g |
| Cobalt chloride hexahydrate | 0.25 g |
| Glucose | 10.00 g |
| Xylose | 14.00 g |
| Sorbitol | 8.00 g |

The solution is adjusted to pH 7.0 with sodium hydroxide.

The pH range suitable for the cultivation of the mutants used in the present invention is about 5.5–7.5, preferably 6–7. The temperature is expediently 25°–40° C., preferably 29°–31° C.

The formation of glucose-isomerase with the mutants of Streptomyces glaucescens NRRL B-2900 used in the present invention may be induced by the addition of xylose to the nutrient medium. Other inductors which can be used in place of xylose are xylanes and polysaccharides synthesised (build up) from xylose, which are widespread in nature, since the mutants used in the present invention provide an intrinsic xylanase. Xylanes are contained, for example, in the straw of cereals (15–20%), in sugar-cane press residues (30%), in cotton pods, in coniferous wood (7–12%) and in the wood of deciduous trees (20–25%). By the acidic hydrolysis or enzymatic degradation of xylanes there is obtained xylose, which is considered the preferred induction agent because in the acidic hydrolysis of xylanes undesired side-products such as furfural, hydroxymethylfurfural and levulinic acid result, which are partially toxic for the microorganisms and which can influence the glucose-isomerase production. For the induction of the glucose-isomerase formation, 0.5–2.0% of xylose is expediently added to the nutrient medium.

The microorganisms may be cultivated in short fermentation times (e.g. 18–30 hours) such that yields of 17–24 units of intra-cellular glucose-isomerase/ml of culture broth are produced. One unit (U) is thus that amount of enzyme which at 70° C., at pH 7.0 and in a 10% glucose solution in 0.05-M phosphate buffer, which is 0.001-M with respect to cobalt chloride hexahydrate and magnesium sulphate heptahydrate, converts 1μ mol of glucose into 1μ mol of fructose in 1 minute.

The glucose-isomerase formed from the mutants of Streptomyces glaucescens NRRL B-2900 is present intra- and extra-cellularly with, as mentioned earlier, an extremely large intra-cellular portion. The intra-cellular portion can amount after 30 hours growth of the mycelium to, for example, up to 95% (with respect to the total glucose-isomerase).

An isolation of the glucose-isomerase formed can be carried out in a manner known per se. The glucose-isomerase can be obtained from the culture filtrate in a simple manner by precipitation, preferably with acetone or ethanol, and centrifuging. After washing with 75% ethanol, it can be dried. Usually, however, it is taken up in a buffer solution, preferably a 0.05-M phosphate buffer of pH 5–8, preferably pH 6.5–7.0. The isolation of the intra-cellular glucose-isomerase portion requires a previous disintegration of the cells. This can be carried out in a manner known per se (e.g. by ultrasonic treatment, the mycelium being disintegrated, or by pressure treatment, for example using a French press). The mixture is subsequently centrifuged in a high-speed centrifuge (12–15,000 r.p.m.) at a low temperature (0°–4° C.), very good yields of glucose-isomerase being obtained.

The glucose-isomerase formed is, however, advantageously not isolated, but rather the mycelium is separated from the culture broth after completion of the fermentation; for example, by vacuum filtration or preferably by centrifuging. After washing with 0.05-M phosphate buffer pH 7.0, it has a beige to white colour.

It is expedient to subject the mycelium to a "heat fixing". This procedure serves to fix the enzyme in the cell (which also functions as the carrier) by which means the enzyme preparation gains significantly in stability. For this purpose, the mycelium is suspended, for example, in a solution of 0.2-M maleate buffer of pH 7.0, 0.00001 to 0.1-M, especially 0.001-M, of cobalt chloride hexahydrate. A 10% suspension of the mycelium is then kept for 30 minutes at a temperature of 70°–75° C.

The cells thus heat-treated in the presence of cobalt ions can now be re-centrifuged and spread on sieves for drying. The drying process is completed, for examle, after 15 hours at 50° C. with the passage of fresh air. Such preparations have high activities, for example 800–1200 U/g, and are very stable. They are very economic in their use since they may be used several times, for example, by centrifuging after each isomerisation. The very good heat stability of the enzyme is remarkable and, because of this, it may be used as temperatures up to 70° C. for the isomerisation of glucose to fructose. Glucose, for example in 50% solution, can be converted at 65° C. into 50% fructose and at 70° C. into 55% fructose.

The isomerisation in accordance with the invention of glucose to fructose by means of glucose-isomerase from the said mutants of Streptomyces glaucescens NRRL B-2900 can be carried out in a manner known per se. Thus, a glucose solution can be treated directly with a culture of the microorganism, i.e. with freshly harvested or (dried and) stored mycelium. On the other hand, the treatment of the glucose can be carried out with the culture filtrate, which contains extra-cellular glucose-isomerase, or with isolated enzyme or with enzyme bonded to a solid carrier.

The isomerisation of glucose to fructose by means of glucose-isomerase from the said mutants of Streptomyces glaucescens NRRL B-2900 can be carried out at a temperature of 55° C. up to 75° C., preferably 60°–65° C., a pH value of 6–9, preferably 6.5–7.0, in order to avoid alkaline side-reactions, and, if desired, in the presence of $Co^{++}$ ions (e.g. 0.00001–0.1, preferably 0.0015 mol/l) and $Mg^{++}$ ions (e.g. 0.001–0.1, preferably 0.01 mol/l). The isomerisation is expediently carried out with a substrate concentration of 30–50%. The fructose formed can be polarometrically determined in the usual manner by measurement of the rotation value of the isomerisation mixture.

The following Examples illustrate the invention:

EXAMPLE 1a

*Streptomyces glaucescens* NRRL B-2900 as well as the mutants of this strain used in accordance with the present invention were cultivated under submerged conditions in the following nutrient medium:

| Yeast extract | 20 g |
|---|---|
| Potassium hydrogen phosphate trihydrate | 0.5 g |
| Magnesium sulphate heptahydrate | 0.25 g |
| Cobalt chloride hexahydrate | 0.25 g |
| Glucose | 10 g |
| Xylose | 14 g |
| Sorbitol | 8 g |

The mixture was made up to a volume of 1 liter with distilled water and the pH value was adjusted to 7 with dilute sodium hydroxide.

The inoculated culture media (70 ml each) were incubated at 30° C. for 46 hours in 250 ml Erlenmeyer flasks having a baffle plate, and at a shaking frequency of 200 revolutions per minute.

Table 1

Yields of glucose-isomerase obtained:

| Strain designation | Melanine formation | Tyrosinase intra-cellular, specific activity U/mg of protein (disintegrated cells) | Glucose-isomerase | | | Portion of extra-cellular glucose-isomerase with respect to the total amount of enzyme (%) |
|---|---|---|---|---|---|---|
| | | | intra-cellular U/ml | extra-cellular U/ml | total U/ml | |
| Str. glauc. NRRL B-2900 | + | 1.0 | 5.4 | 1.9 | 7.3 | 26 |
| Str. glauc. NRRL 8071 | — | <0.01 | 11.8 | 1.1 | 12.9 | 8.5 |
| Str. glauc. NRRL 8072 | — | <0.01 | 6.4 | 0.6 | 7.0 | 6.8 |
| Str. glauc. NRRL 8073 | — | <0.01 | 8.4 | 0.2 | 8.6 | 2.3 |
| Str. glauc. NRRL 8074 | — | <0.01 | 9.6 | 0.7 | 10.3 | 6.8 |

Determination of the tyrosinase activity with the dopachrome test according to Lerch: Eur. J. Biochim. 31, 427–437 (1972)

EXAMPLE 1b

Production of glucose-isomerase with *Streptomyces glaucescens* NRRL 8071 using xylane.

The nutrient medium has the following composition:

| | Parts by weight/litre |
|---|---|
| Yeast extract | 20 g |
| Magnesium sulphate heptahydrate | 0.25 g |
| Cobalt chloride hexahydrate | 0.24 g |
| Potassium hydrogen phosphate trihydrate | 0.50 g |
| Xylane | 10 g |
| Starch | 10 g |
| Sorbitol | 8 g |

The medium was adjusted to pH 6.5. The cultures, 70 ml each per 250 ml Erlenmeyer flask, were incubated for 24 hours at a shaking frequency of 200 revolutions per minute and at 30° C.

There were obtained 5 units of intra-cellular glucose-isomerase/ml of culture medium.

EXAMPLE 2

A fermenter was charged with 10 liters of a nutrient medium of the following composition containing a 10% inoculation culture of *Streptomyces glaucescens* NRRL 8071 which was cultured in a shaking flask at 30° C. and at 200 revolutions per minute.

| Nutrient medium | Parts by weight/litre |
|---|---|
| Yeast extract | 20 g |
| Potassium hydrogen phosphate trihydrate | 0.5 g |
| Magnesium sulphate heptahydrate | 0.25 g |
| Cobalt chloride hexahydrate | 0.25 g |
| Sorbitol | 8 g |
| Xylose | 6 g |
| Glucose | 6 g |

The volume was brought up to 10 liters with distilled water and the pH value adjusted to 7 by means of dilute sodium hydroxide solution. The aeration amounted to 1 VVM (1 volume of air/volume of medium and minutes).

The medium for the inoculation culture had the same composition.

The cultivation was carried out at 30° C. with constant stirring by means of two flat blade stirrers. During the fermentation, small amounts of glucose were continuously added. After 22 hours, the enzyme production achieved its maximum with 17 units/ml of culture broth.

After completion of the fermentation, the mycelium was separated by centrifuging the nutrient medium, washed and deep-frozen.

EXAMPLE 3

The production of the enzyme was carried out with a nutrient medium having the following composition:

| Solid material ex maize spring water | 20 g |
|---|---|
| Yeast extract | 5 g |
| Potassium hydrogen phosphate trihyddrate | 0.5 g |
| Magnesium sulphate heptahydrate | 0.25 g |
| Cobalt chloride hexahydrate | 0.24 g |
| Sorbitol | 8 g |
| Glucose | 6 g |
| Xylose | 14 g |
| Magnesium hydroxide carbonate | 2.5 g |

The volume was brought up to 1 liter with distilled water and the pH value adjusted to 7 by means of dilute sodium hydroxide solution.

The inoculation culture (10%) originated from the fermenter test described in Example 2. The test conditions were the same as in the previous Example. Magnesium hydroxide carbonate was added to neutralise the acid formed. After 18 hours, 20 U/ml of culture broth or 250 U/g of mycelium (wet weight) were measured at a pH value of 7.3.

EXAMPLE 4

30 liters of nutrient medium and an inoculation culture of *Streptomyces glaucescens* NRRL 8071 (10%) were introduced into a 50 liter fermenter.

The composition of the medium was as follows:

| | |
|---|---|
| Yeast extract | 20 g |
| Potassium hydrogen phosphate trihydrate | 0.5 g |
| Magnesium sulphate heptahydrate | 0.25 g |
| Cobalt chloride hexahydrate | 0.25 g |
| Glucose | 10 g |
| Xylose | 14 g |
| Sorbitol | 8 g |

The mixture was made up to 1 liter with distilled water. The pH was 7.

The fermenter was equipped with two flat blade stirrers. 30 liters of air were blown through the nutrient solution per minute. The temperature was held at 30° C. and the contents rotated at 750 revolutions per minute. Silicon-defoamer (Merck) was added for foam control.

After fermentation for 46 hours, a biomass of 2850 kg was obtained. The pH value was 8.5. 24 units of glucose-isomerase were obtained per 1 ml of fermentation broth. 1 g of cell mass (wet weight) accordingly contained 252 U. The mycelium was partly subjected directly in the fermenter to a 30 minute heat-treatment at 70° C. in the presence of cobalt chloride, 0.001 mol/l, partly washed and heat-treated (70° C.) in 0.2-M maleate buffer of pH 7.0, 0.001 molar in cobalt chloride hexahydrate.

The centrifuged cells were dried at 50° C. while passing through fresh air. A preparation of 1200 U/g of dry substance was obtained.

The preparation also has no loss of activity after storage for 1 year at room temperature.

EXAMPLE 5

12.5 ml glass flasks provided with ground stoppers were charged with 5 ml of a mixture, containing a substrate solution having the following composition:

| | | |
|---|---|---|
| Glucose | 50 | g |
| Cobalt chloride hexahydrate | 0.024 | g |
| Magnesium sulphate heptahydrate | 0.025 | g |
| 0.2-M maleate buffer pH 7 ad | 100 | ml | and 25 mg of the dry substance of an enzyme preparation, and shaken in a water-bath for 19 hours at 65° C. After completion of the isomerisation, the cells were centrifuged off and the content of fructose was determined by means of optical rotation.

The cells were again taken up in 5 ml of fresh substrate solution and further isomerisation were carried out.

The result was as follows:

Table 2

| Number of cycles of 19 hours | Enzyme preparation of Str. glauc. NRRL 8071* | |
|---|---|---|
| | % Isomerisation | % Loss with respect to previous isomerisation |
| 1st Isomerisation | 40 | 0 |
| 2nd Isomerisation | 38 | 5 |
| 3rd Isomerisation | 37 | 2.7 |
| 4th Isomerisation | 26 | 30 |
| 5th Isomerisation | 20 | 23 |

The pH value decreased by 0.45 units per cycle.
*Activity [Streptomyces glauc. NRRL 8071]: 1200 U/g of dry substance.

EXAMPLE 6

The activity of Streptomyces glaucescens NRRL 8071 (which only fell slowly) with multiple use under non-oxidative conditions was ascertained as follows:

A corresponding mixture was in each case stirred for 19 hous at 65° C. under argon. The composition of the substrate solution and the enzyme dosage were the same as given in Example 5.

Table 3

| | Streptomyces glaucescens NRRL 8071 | |
|---|---|---|
| Number of cycles (each 19 hours) | % Isomerisation | % Decrease with respect to previous isomerisation |
| 1st Isomerisation | 48 | |
| 2nd Isomerisation | 48 | 0 |
| 3rd Isomerisation | 48 | 0 |
| 4th Isomerisation | 48 | 0 |
| 5th Isomerisation | 43 | 10 |
| 6th Isomerisation | 38 | 12 |
| 7th Isomerisation | 37 | 3 |
| 8th Isomerisation | 31 | 16 |
| 9th Isomerisation | 28 | 10 |
| 10th Isomerisation | 26 | 7 |
| 11th Isomerisation | 25 | 4 |
| 12th Isomerisation | 23 | 8 |

The pH value only decreased from 7.0 to 6.8 per cycle.

What is claimed is:

1. A process for the manufacture of a glucose-isomerase, which comprises cultivating under aerobic conditions a mutant of Streptomyces glaucescens NRRL B-2900 having no or practically no intra-cellular tyrosinase activity in a nutrient medium containing a source of assimilable carbon and a source of assimilable nitrogen.

2. A process according to claim 1, wherein the glucose-isomerase is isolated.

3. A process according to claim 1, wherein the nutrient medium contains as the induction agent xylose or a polysaccharide degradable to xylose by the microorganism.

4. A process according to claim 1, wherein Streptomyces glaucescens NRRL 8071, 8072, 8073 or 8074 is used as the microorganism.

5. A process according to claim 2, wherein the nutrient medium contains as the induction agent xylose or a polysaccharide degradable to xylose by the microorganism.

6. A process according to claim 1, wherein said process is conducted at a temperature from about 25° C. to about 40° C. and a pH between the range from about 5.5 to about 7.5.

7. A process according to claim 6 wherein the glucose-isomerase is isolated.

8. A process according to claim 7, wherein the nutrient medium contains as the induction agent xylose or a polysaccharide degradable to xylose by the microorganism.

9. A process according to claim 6, wherein the nutrient medium contains as the induction agent xylose or a polysaccharide degradable to xylose by the microorganism.

10. A process according to claim 6, wherein Streptomyces glaucescens NRRL 8071, 8072, 8073 or 8074 is used as the microorganism.